United States Patent
Wolf et al.

(10) Patent No.: US 8,344,157 B2
(45) Date of Patent: Jan. 1, 2013

(54) PROCESS FOR PREPARING 1,3-DISUBSTITUTED PYRAZOLECARBOXYLIC ESTERS

(75) Inventors: Bernd Wolf, Fussgoenheim (DE); Sebastian Peer Smidt, Oftersheim (DE); Volker Maywald, Ludwigshafen (DE); Christopher Koradin, Ludwigshafen (DE); Michael Keil, Freinsheim (DE); Thomas Zierke, Boehl-Iggelheim (DE); Michael Rack, Eppelheim (DE)

(73) Assignee: BASF SE, Ludwigshafen (DE)

( * ) Notice: Subject to any disclaimer, the term of this patent is extended or adjusted under 35 U.S.C. 154(b) by 38 days.

(21) Appl. No.: 13/054,642

(22) PCT Filed: Jul. 10, 2009

(86) PCT No.: PCT/EP2009/058854
§ 371 (c)(1),
(2), (4) Date: Jan. 18, 2011

(87) PCT Pub. No.: WO2010/009990
PCT Pub. Date: Jan. 28, 2010

(65) Prior Publication Data
US 2011/0118474 A1    May 19, 2011

(30) Foreign Application Priority Data
Jul. 21, 2008    (EP) ..................... 08160833

(51) Int. Cl.
C07D 231/10    (2006.01)
(52) U.S. Cl. ................................... 548/374.1
(58) Field of Classification Search ........... 548/374.1
See application file for complete search history.

(56) References Cited

U.S. PATENT DOCUMENTS

| | | | |
|---|---|---|---|
| 5,093,347 A | 3/1992 | Graneto et al. | |
| 5,330,995 A | 7/1994 | Eicken et al. | |
| 5,340,837 A | 8/1994 | Hall et al. | |
| 5,438,070 A | 8/1995 | Eicken et al. | |
| 5,498,624 A | 3/1996 | McLoughlin et al. | |
| 5,618,951 A | 4/1997 | Britton | |
| 6,706,911 B1 | 3/2004 | Lui et al. | |
| 7,358,387 B2 | 4/2008 | Lantzsch et al. | |
| 7,388,097 B2 | 6/2008 | Elbe et al. | |
| 7,501,527 B2 | 3/2009 | Lantzsch et al. | |
| 7,521,397 B2 | 4/2009 | Dunkel et al. | |
| 7,585,998 B2 | 9/2009 | Gallenkamp et al. | |
| 7,863,460 B2* | 1/2011 | Aihara et al. | 548/374.1 |
| 7,939,673 B2 | 5/2011 | Pazenok et al. | |
| 7,994,207 B2* | 8/2011 | Zierke et al. | 514/403 |
| 8,115,012 B2* | 2/2012 | Sukopp et al. | 548/374.1 |
| 2008/0108686 A1 | 5/2008 | Gewehr et al. | |
| 2009/0105316 A1 | 4/2009 | Dunkel et al. | |
| 2010/0069646 A1 | 3/2010 | Sukopp et al. | |
| 2010/0174094 A1 | 7/2010 | Zierke et al. | |
| 2010/0184994 A1 | 7/2010 | Nett et al. | |
| 2010/0204483 A1 | 8/2010 | Pazenok et al. | |
| 2010/0215777 A1 | 8/2010 | Pohlman et al. | |
| 2010/0274049 A1 | 10/2010 | Lui et al. | |
| 2011/0040096 A1 | 2/2011 | Zierke et al. | |
| 2011/0046371 A1 | 2/2011 | Zierke et al. | |
| 2011/0172436 A1 | 7/2011 | Wolf et al. | |

FOREIGN PATENT DOCUMENTS

| | | |
|---|---|---|
| EP | 0545099 | 6/1993 |
| EP | 0581725 | 2/1994 |
| EP | 0589301 | 3/1994 |
| EP | 1854788 | 11/2007 |
| EP | 2 042 482 | 4/2009 |
| EP | 2 072 497 | 6/2009 |
| JP | 266612 | 2/1989 |
| JP | 2000/212166 | 8/2000 |

(Continued)

OTHER PUBLICATIONS

Nagarajan et al (1986), Journal of Chemical Research, Synopses, vol (5), 166-7, 1986.*

(Continued)

*Primary Examiner* — Golam M M Shameem
(74) *Attorney, Agent, or Firm* — Brinks Hofer Gilson & Lione

(57) ABSTRACT

A process for preparing 1,3-disubstituted pyrazolecarboxylic esters of the formula (I)

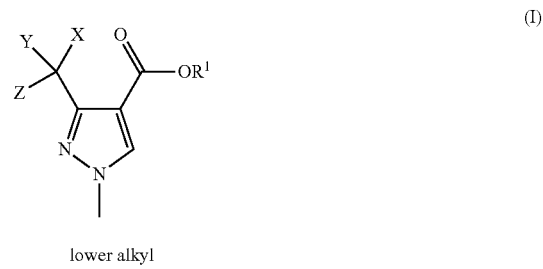

where
X, Y, Z=hydrogen or halogen and
$R^1=C_1-C_6$-alkyl,
by metering an enol ether of the formula III

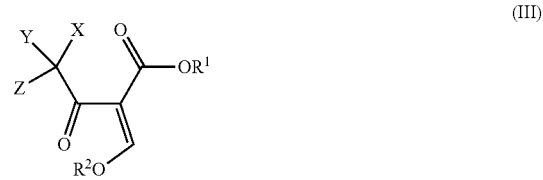

where $R^2$ is $C_1-C_6$-alkyl at from (−41) to (−80)° C. into an alkyl hydrazine of the formula II H$_2$N—NH-lower alkyl    (II).

7 Claims, No Drawings

FOREIGN PATENT DOCUMENTS

| | | |
|---|---|---|
| WO | WO 92/12970 | 8/1992 |
| WO | WO 93/11117 | 6/1993 |
| WO | WO 03/051820 | 6/2003 |
| WO | WO 03/066610 | 8/2003 |
| WO | WO 03/070705 | 8/2003 |
| WO | WO 2005/003077 | 1/2005 |
| WO | WO 2005/042468 | 5/2005 |
| WO | WO 2005/044804 | 5/2005 |
| WO | WO 2005/123690 | 12/2005 |
| WO | WO 2006/024389 | 3/2006 |
| WO | WO 2006/090778 | 8/2006 |
| WO | WO 2007/003603 | 1/2007 |
| WO | WO 2007/006806 | 1/2007 |
| WO | WO 2007/031323 | 3/2007 |
| WO | WO 2008/022777 | 2/2008 |
| WO | WO 2008/053043 | 5/2008 |
| WO | WO 2008/077907 | 7/2008 |
| WO | WO 2008/113660 | 9/2008 |
| WO | WO 2008/145740 | 12/2008 |
| WO | WO 2008/152138 | 12/2008 |
| WO | WO 2009/133178 | 11/2009 |
| WO | WO 2009/133179 | 11/2009 |
| WO | WO 2009/135808 | 11/2009 |

OTHER PUBLICATIONS

Toshio et al (2000), Jpn. Kokai Tokkyo Koho, 2000212166, Aug. 2, 2000.*

International Search Report for International Application No. PCT/EP2009/058854.

International Preliminary Report on Patentability for International Application No. PCT/EP2009/058854.

Altenbach, Robert J. et al., "Synthesis, Potency, and In Vivo Profiles of Quinoline Containing Histamine $H_3$ Receptor Inverse Agonists", J. Med. Chem., vol. 50, 2007, pp. 5439-5448.

Etsuji, Okada, et al., "Facile synthetic methods for 3- and 5-trifluoromethyl-4-trifluoroacetyl-pyrazoles and their conversion into pyrazole-4-carobxylic acids", Heterocycles, vol. 34, No. 4, 1992, pp. 791-798.

Pryadeina, M.V. et al., "Synthesis and Structure of 2-ethoxy- and 2-aminomethylidene 3-fluoroalkyl-3-oxopropionates," Russian Journal of Organic Chemistry, vol. 43, No. 7, 2007, pp. 945-955 (XP002557997).

Vinogradova, N. B., et al., "Synthesis and Mechanism of the Formation of Bis(Methylamides) of Pyrazoledicarboxylic Acids, Chemistry of Heterocyclic Compounds", Jan. 1, 1968, vol. 4, pp. 502-507.

* cited by examiner

PROCESS FOR PREPARING 1,3-DISUBSTITUTED PYRAZOLECARBOXYLIC ESTERS

This application is a National Stage application of International Application No. PCT/EP2009/058854 filed Jul. 10, 2009, the entire contents of which is hereby incorporated herein by reference. This application also claims priority under 35 U.S.C. §119 to European Patent Application No. 08160833.3, filed Jul. 21, 2008, the entire contents of which is hereby incorporated herein by reference.

The present invention relates to a process for preparing 1,3-disubstituted pyrazolecarboxylic esters of the formula (I)

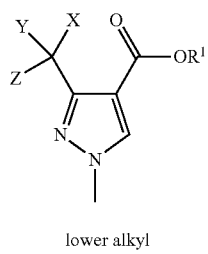

where
X, Y, Z are each hydrogen or halogen and
$R^1$ is $C_1$-$C_6$-alkyl,
which comprises metering an enol ether of the formula III

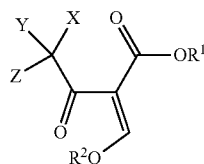

where $R^2$ is $C_1$-$C_6$-alkyl at from (−41) to (−80)° C. into an alkyl hydrazine of the formula II $$H_2N\text{—}NH\text{-lower alkyl} \qquad (II).$$

Typically, the pyrazole ester synthesis is effected within the temperature range from +25 to (−15)° C. (cf., for example, WO 2005/003077, U.S. Pat. No. 5,498,624, U.S. Pat. No. 5,093,347, JP-A 2000/212166, WO 2006/090778, JP 01113371).

In addition, WO 2005/123690 (see preparation example) describes the synthesis of ethyl 3-difluoromethyl-1-methyl-1H-pyrazole-4-carboxylate at (−40)° C.

In the syntheses known to date for preparing 1,3-disubstituted pyrazole-4-carboxylic esters, more than 10% of the isomeric 1,5-disubstituted pyrazole-4-carboxylic acid derivatives VI is always also obtained

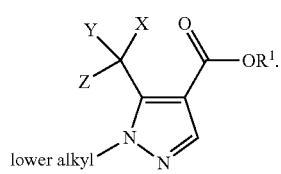

The purification of the products of value I (i.e. the removal of the isomer VI) is found to be very complicated and the yields are accordingly low.

It was accordingly an object of the invention to provide a process usable on the industrial scale for substantially isomerically pure preparation of the 1,3-disubstituted pyrazolecarboxylic esters I.

Accordingly, it has been found that the 1,3-disubstituted pyrazolecarboxylic esters I are obtainable in high yields and with an isomeric purity of more than 6.5:1, by metering an enol ether III into an alkyl hydrazine II at from (−41) to (−80)° C.

The alkyl hydrazines II are commercially available. They can be used in pure form or as an aqueous solution (e.g. 35%). However, even greater amounts of water should be avoided, since the isomer ratio otherwise worsens again.

The enol ethers III are generally obtainable according to WO 2005/003077.

The term "halogen" denotes in each case fluorine, chlorine, bromine or iodine, preferably fluorine or chlorine.

"Lower alkyl" represents methyl, ethyl, propyl, 1-methylethyl, butyl, 1-methylpropyl, 2-methylpropyl and 1,1-dimethylethyl, especially methyl.

"$C_1$-$C_6$-Alkyl", as used herein, denotes a saturated, straight-chain or branched hydrocarbon group comprising from 1 to 6 carbon atoms, especially from 1 to 4 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethyl-butyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and isomers thereof. $C_1$-$C_4$-Alkyl comprises, for example, methyl, ethyl, propyl, 1-methylethyl, butyl, 1-methylpropyl, 2-methylpropyl or 1,1-dimethylethyl.

The preparation of ethyl 3-difluoromethyl-1-methyl-1H-pyrazole-4-carboxylate is very particularly preferred.

According to the invention, the reaction is conducted at from (−41) to (−80)° C., especially at from (−50) to (−60)° C.

The alkyl hydrazine II is advantageously cooled to the reaction temperature in a solvent or diluent and then the enol ether III is metered in. The reverse metering sequence generally affords significantly poorer isomeric ratios.

The enol ether III is preferably used in undiluted form or dissolved in the organic solvent in which (II) has also been initially charged. The metered addition of III is generally effected over the course of from 0.58 to 20 hours, especially from 2 to 10 hours.

The alkyl hydrazines II can be used in pure form or as an aqueous solution (e.g. 35%). However, even greater amounts of water should be avoided, since the isomer ratio otherwise worsens again.

Usable solvents are lower alcohols, especially ethanol. For reasons of stability, it is advisable to freshly prepare the solution of enol ether III and the alcohol used only shortly before the metered addition.

In the case of metering times of more than 2 hours, the undiluted metered addition of III is advantageous.

Enol ether I and alkyl hydrazine II are typically used in about equimolar amounts, but it is also possible to use one component in a small excess, up to about 30 mol %.

Advantageously, the alkyl hydrazine is used in excess; preference is given to 1.05-1.3 molar equivalents.

It is normal to work at atmospheric pressure or under the autogenous pressure of the reaction mixture.

The pyrazole-4-carboxylic esters I formed can be purified in a customary manner (e.g. distillation, crystallization, etc), or be converted further as crude products (if appropriate dissolved in a solvent).

In a preferred embodiment of the process, the crude pyrazole ester solution without intermediate purification is hydrolyzed to the pyrazole carboxylic acid IV, for example according to WO 2005/123690 or U.S. Pat. No. 5,498,624. Only at the acid stage is the 1,3-disubstituted pyrazole-4-carboxylic acid IV purified and isolated by precipitation and filtration.

The 1,3-disubstituted pyrazole-4-carboxylic esters I and 1,3-disubstituted pyrazole-4-carboxylic acids IV are valuable active ingredients in crop protection. They serve, for example, to prepare pyrazolylcarboxamides of the formula V

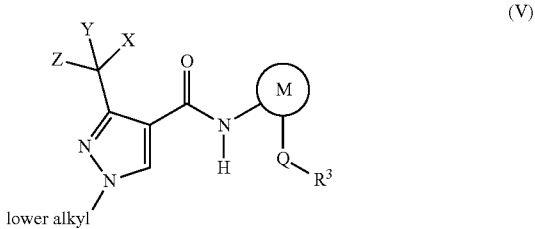

(V)

where the substituents are each defined as follows:
M is thienyl or phenyl which may bear a halogen substituent;
Q is a direct bond, cyclopropylene, or a fused bicyclo[2.2.1]heptane-or bicyclo[2.2.1]heptene ring;
$R^3$ is hydrogen, halogen, $C_1$-$C_6$-alkyl, $C_1$-$C_4$-alkoxy, $C_1$-$C_4$-haloalkoxy, mono- to trisubstituted phenyl, where the substituents are each independently selected from halogen and trifluoromethylthio, or cyclopropyl.

Preferred arylcarboxamides V are penthiopyrad, bixafen, N-(3',4',5'-trifluorobiphenyl-2-yl)-3-difluoromethyl-1-methylpyrazole-4-yl-carboxamide, N-(2-bicyclopropyl-2-ylphenyl)-3-difluoromethyl-1-methylpyrazol-4-yl-carboxamide (common name: sedaxane) and 3-(difluoromethyl)-1-methyl-N-[1,2,3,4-tetrahydro-9-(1-methylethyl)-1,4-methanonaphthalen-5-yl]-1H-pyrazol-4-yl-carboxamide (common name: isopyrazam).

PREPARATION EXAMPLES

Example 1 (Inventive)

Preparation of ethyl 3-difluoromethyl-1-methyl-1H-pyrazole-4-carboxylate at (−60)° C. and subsequent hydrolysis to 3-difluoromethyl-1-methyl-1H-pyrazole-4-carboxylic acid.

43.8 g (0.33 mol) of methylhydrazine solution (34.7% by weight of methylhydrazine in water) and 270 g of ethanol (anhydrous, undenatured) were initially charged and cooled to (−60)° C. Within 2 hours, at (−60)° C., a freshly prepared solution of 71.1 g (0.3 mol) of ethyl 2-ethoxymethylene-4,4-difluoro-3-oxobutyrate (93.7%) in 71 g of ethanol was added dropwise. This formed a suspension which was stirred at (−60)° C. for another hour and then warmed to 25-30° C. within 3 hours. The solution comprised 11.18% by weight of the desired ethyl 3-difluoromethyl 1-methyl-1H-pyrazole-4-carboxylate and only 1.14% by weight of the undesired isomeric ethyl 5-difluoromethyl-1-methyl-1H-pyrazole-4-carboxylate (HPLC analysis, quantification with external standard). The isomer ratio was 9.8:1.

252.5 g (0.45 mol) of 10% aqueous potassium hydroxide solution were metered and the reaction mixture was stirred at 60° C. for 3 hours. The solvent was then distilled off completely under reduced pressure and the remaining residue dissolved in 480 g of demineralized water. 100 g (0.877 mol) of conc. hydrochloric acid (32%) were added dropwise to the salt solution at 55° C. within 20 minutes, in the course of which the desired carboxylic acid crystallized out. The suspension was cooled to 3° C. and stirred at this temperature for a further 1 hour. The solid was filtered off and washed twice with 100 g of cold demineralized water (3° C.). After the drying (60° C., 20 mbar), 45.1 g of 3-difluoromethyl-1-methyl-1H-pyrazole-4-carboxylic acid were obtained in a purity of 98.6% by weight. The yield, based on the molar amount of ethyl 2-ethoxymethylene-4,4-difluoro-3-oxobutyrate used, was 84.2%.

Example 2 (Comparative Example)

Preparation of ethyl 3-difluoromethyl-1-methyl-1H-pyrazole-4-carboxylate at (−40)° C. and subsequent hydrolysis to 3-difluoromethyl-1-methyl-1H-pyrazole-4-carboxylic acid 43.8 g (0.33 mol) of methylhydrazine solution (34.7% by weight of methylhydrazine in water) and 270 g of ethanol (anhydrous, undenatured) were initially charged and cooled to (−40)° C. Within 2 hours, at (−40)° C., a freshly prepared solution of 71.1 g (0.3 mol) of ethyl 2-ethoxymethylene-4,4-difluoro-3-oxobutyrate (93.7%) in 71 g of ethanol was added dropwise. This formed a suspension which was stirred at (−40)° C. for another hour and then warmed to 25-30° C. within 1 hour. The solution comprised 10.45% by weight of the desired ethyl 3-difluoromethyl 1-methyl-1H-pyrazole-4-carboxylate and 1.6% by weight of the undesired isomeric ethyl 5-difluoromethyl-1-methyl-1H-pyrazole-4-carboxylate (HPLC analysis, quantification with external standard). The isomer ratio was 6.5:1.

252.5 g (0.45 mol) of 10% aqueous potassium hydroxide solution were metered and the reaction mixture was stirred at 60° C. for 3 hours. The solvent was then distilled off completely under reduced pressure and the remaining residue dissolved in 480 g of demineralized water. 100 g (0.877 mol) of conc. hydrochloric acid (32%) were added dropwise to the salt solution at 55° C. within 20 minutes, in the course of which the desired carboxylic acid crystallized out. The suspension was cooled to 3° C. and stirred at this temperature for a further 1 hour. The solid was filtered off and washed twice with 100 g of cold demineralized water (3° C.). After the drying (60° C., 20 mbar), 42.5 g of 3-difluoromethyl-1-methyl-1H-pyrazole-4-carboxylic acid were obtained in a purity of 98.7% by weight. The yield, based on the molar amount of ethyl 2-ethoxymethylene-4,4-difluoro-3-oxobutyrate used, was 79.4%.

Example 3 (Comparative Example)

Preparation of ethyl 3-difluoromethyl-1-methyl-1H-pyrazole-4-carboxylate at (−20)° C. and subsequent hydrolysis to 3-difluoromethyl-1-methyl-1H-pyrazole-4-carboxylic acid 43.8 g (0.33 mol) of methylhydrazine solution (34.7% by weight of methylhydrazine in water) and 270 g of ethanol (anhydrous, undenatured) were initially charged and cooled to (−20)° C. Within 2 hours, at (−20)° C., a freshly prepared solution of 71.1 g (0.3 mol) of ethyl 2-ethoxymethylene-4,4-difluoro-3-oxobutyrate (93.7%) in 71 g of ethanol was added dropwise. This formed a suspension which was stirred at (−20)° C. for another hour and then warmed to 25-30° C. within 1 hour. The solution comprised 10.05% by weight of the desired ethyl 3-difluoromethyl 1-methyl-1H-pyrazole-4-carboxylate and 2.27% by weight of the undesired isomeric ethyl 5-difluoromethyl-1-methyl-1H-pyrazole-4-carboxylate (HPLC analysis, quantification with external standard). The isomer ratio was 4.4:1.

252.5 g (0.45 mol) of 10% aqueous potassium hydroxide solution were metered and the reaction mixture was stirred at 60° C. for 3 hours. The solvent was then distilled off completely under reduced pressure and the remaining residue dissolved in 480 g of demineralized water. 100 g (0.877 mol) of conc. hydrochloric acid (32%) were added dropwise to the salt solution at 55° C. within 20 minutes, in the course of which the desired carboxylic acid precipitated out. The suspension was cooled to 3° C. and stirred at this temperature for a further 1 hour. The solid was filtered off and washed twice with 100 g of cold demineralized water (3° C.). After the drying (60° C., 20 mbar), 42.3 g of 3-difluoromethyl-1-methyl-1H-pyrazole-4-carboxylic acid were obtained in a purity of 95.0% by weight (4.06% by weight of incorrect isomer). The yield, based on the molar amount of ethyl 2-ethoxymethylene-4,4-difluoro-3-oxobutyrate used, was 76.1%.

Example 4 (Inventive)

Preparation of ethyl 3-difluoromethyl-1-methyl-1H-pyrazole-4-carboxylate at from (−50) to (−60)° C. and subsequent hydrolysis to 3-difluoromethyl-1-methyl-1H-pyrazole-4-carboxylic acid A 400 liter stirred vessel was initially charged with 22.6 kg (172 mol) of methylhydrazine solution (35% by weight of methylhydrazine in water) and 132 kg of ethanol, and cooled to (−55)° C. Within 2.33 hours, at internal temperature from (−50) to (−60)° C., 40.4 kg (172.5 mol) of ethyl 2-ethoxymethylene-4,4-difluoro-3-oxobutyrate (94.8%) were metered in from a reservoir vessel. The reservoir vessel was rinsed out with 9.1 kg of ethanol. The suspension was stirred at (−55)° C. for a further one hour and then the vessel contents were heated to 25° C. within 4 hours. 102.3 kg (255.75 mol) of 10% sodium hydroxide solution were metered in within 45 minutes, the feed line was rinsed out with 10 liters of demineralized water and the reaction mixture was stirred at 60° C. for 3 hours. After cooling to 25° C., the pressure was reduced stepwise down to 50 mbar. In the course of slow heating to internal temperature 42° C., a total of 180 liters of ethanol/water were distilled off. 300 liters of water were fed and the reaction mixture was cooled to 10° C. At this temperature, 47.8 kg (419 mol) of hydrochloric acid (32%) were metered in within one hour. After the feed line had been rinsed with 10 liters of water, the resulting suspension was stirred at 25° C. for 12 hours. The solids were then filtered off in portions through a pressure filter and the filtercake was washed with 30 liters of demineralized water (with stirring). The solids were substantially freed of liquid by injecting 2.5 bar of nitrogen and, after discharge, dried in a drying cabinet (35-40° C., 25 mbar). After drying, 25.1 kg of 3-difluoromethyl-1-methyl-1H-pyrazole-4-carboxylic acid were obtained in a purity of 99.6% (GC area %). The yield, based on the molar amount of methylhydrazine used, was 82.6%.

The invention claimed is:

1. A process for preparing 1,3-disubstituted pyrazolecarboxylic esters of the formula I

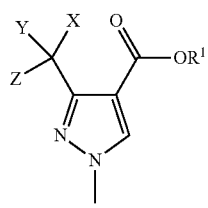

lower alkyl where

X, Y, Z are each hydrogen or halogen and

R$^1$ is C$_1$-C$_6$-alkyl, which comprises metering an enol ether of formula III

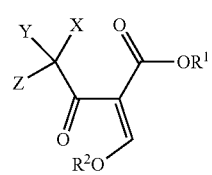

where R$^2$ is C$_1$-C$_6$-alkyl at from −41 to −80° C. into an alkyl hydrazine of formula II

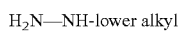

H$_2$N—NH-lower alkyl    (II).

2. The process of claim 1, wherein X and Y are each fluorine or chlorine and Z is hydrogen.

3. The process of claim 1, wherein the metering of the enol ether of formula III into the alkyl hydrazine of formula II is undertaken in a lower alcohol.

4. The process of claim 1, wherein from 1.05 to 1.3 molar equivalents of the alkyl hydrazine of formula II, based on the amount of the enol ether of formula III, are used.

5. The process of claim 1, wherein the metering of the enol ether of formula III into the alkyl hydrazine of formula II is undertaken at from −50 to −60° C.

6. A process for preparing 1,3-disubstituted pyrazolecarboxylic acids of formula IV

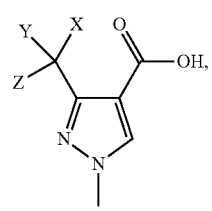

lower alkyl where X, Y and Z are each hydrogen or halogen, which comprises a) preparing a 1,3-disubstituted pyrazolecarboxylic ester of formula I according to claim 1 and b) converting the 1,3-disubstituted pyrazolecarboxylic ester of formula I to the 1,3-disubstituted pyrazolecarboxylic acids of formula IV.

7. The process of claim 1, wherein said metering is conducted at a temperature of −50 to −80 ° C.

* * * * *